(12) United States Patent
Edquist et al.

(10) Patent No.: US 11,480,329 B2
(45) Date of Patent: Oct. 25, 2022

(54) LIGHTING UNITS PRODUCING VISIBLE LIGHT WITH BLENDED DISINFECTING ELECTROMAGNETIC RADIATION

(71) Applicant: B/E AEROSPACE, INC., Winston Salem, NC (US)

(72) Inventors: John Edquist, Miwaukee, WI (US); Eric Johannessen, Holbrook, NY (US)

(73) Assignee: B/E Aerospace, Inc., Winston Salem, NC (US)

( * ) Notice: Subject to any disclaimer, the term of this patent is extended or adjusted under 35 U.S.C. 154(b) by 141 days.

(21) Appl. No.: 17/027,496

(22) Filed: Sep. 21, 2020

(65) Prior Publication Data
US 2022/0090777 A1 Mar. 24, 2022

(51) Int. Cl.
| | | |
|---|---|---|
| *F21V 33/00* | (2006.01) | |
| *F21V 3/06* | (2018.01) | |
| *H05B 45/10* | (2020.01) | |
| *A61L 2/10* | (2006.01) | |
| *A61L 2/24* | (2006.01) | |
| *B64D 47/02* | (2006.01) | |
| *F21V 19/00* | (2006.01) | |
| *F21V 23/00* | (2015.01) | |

(Continued)

(52) U.S. Cl.
CPC ............ *F21V 33/0064* (2013.01); *A61L 2/10* (2013.01); *A61L 2/24* (2013.01); *B64D 47/02* (2013.01); *F21V 3/06* (2018.02); *F21V 19/0015* (2013.01); *F21V 23/003* (2013.01); *H05B 45/10* (2020.01); *A61L 2202/11* (2013.01); *A61L 2202/14* (2013.01); *A61L 2202/25* (2013.01); *B64D 2203/00* (2013.01); *F21W 2106/00* (2018.01); *F21W 2107/30* (2018.01); *F21Y 2115/10* (2016.08)

(58) Field of Classification Search
None
See application file for complete search history.

(56) References Cited

U.S. PATENT DOCUMENTS

| | | |
|---|---|---|
| 8,398,264 B2 | 3/2013 | Anderson et al. |
| 9,039,966 B2 | 5/2015 | Anderson et al. |

(Continued)

FOREIGN PATENT DOCUMENTS

KR 20200036111 4/2020

OTHER PUBLICATIONS

European Patent Office; Extended European Search Report dated Feb. 17, 2022 in Application No. 21197795.5.

*Primary Examiner* — Britt D Hanley
(74) *Attorney, Agent, or Firm* — Snell & Wilmer L.L.P.

(57) ABSTRACT

A lighting unit may include a first light-emitting diode ("LED"), a second LED, and a third LED. The first LED may be configured to emit first electromagnetic radiation having a first wavelength of between about 600 nanometers ("nm") and about 740 nm, the second LED may be configured to emit second electromagnetic radiation having a second wavelength of between about 500 nm and about 565 nm, and the third LED may be configured to emit third electromagnetic radiation having a third wavelength between about 315 nm and about 430 nm. Thus, the third electromagnetic radiation may be disinfecting UV-A radiation that is incorporated into a lighting unit that produces visible light.

7 Claims, 5 Drawing Sheets
(1 of 5 Drawing Sheet(s) Filed in Color)

(51) Int. Cl.
  *F21Y 115/10* (2016.01)
  *F21W 107/30* (2018.01)
  *F21W 106/00* (2018.01)

(56) References Cited

U.S. PATENT DOCUMENTS

| | | |
|---|---|---|
| 9,839,706 B2 | 12/2017 | Anderson et al. |
| 10,413,626 B1 | 9/2019 | Barron et al. |
| 10,433,389 B2 | 10/2019 | Paulsen et al. |
| 2006/0023463 A1 | 2/2006 | Bigge et al. |
| 2016/0016001 A1 | 1/2016 | Loupis et al. |
| 2018/0147417 A1 | 5/2018 | Rantala |
| 2018/0311386 A1* | 11/2018 | Hawkins ............. F21V 33/0068 |
| 2019/0030195 A1* | 1/2019 | Hatti ..................... A61L 2/24 |
| 2020/0222718 A1 | 7/2020 | Enwemeka et al. |

* cited by examiner

FIG. 6 dr# LIGHTING UNITS PRODUCING VISIBLE LIGHT WITH BLENDED DISINFECTING ELECTROMAGNETIC RADIATION

FIELD

The present disclosure relates to devices, systems, and methods for pathogen disinfection, and in particular to incorporating disinfecting electromagnetic radiation into visible light emitted from a lighting unit.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

In various embodiments, the present disclosure provides a lighting unit comprising a first light-emitting diode ("LED"), a second LED, and a third LED. The first LED may be configured to emit first electromagnetic radiation having a first wavelength of between about 600 nanometers ("nm") and about 740 nm, the second LED may be configured to emit second electromagnetic radiation having a second wavelength of between about 500 nm and about 565 nm, and the third LED may be configured to emit third electromagnetic radiation having a third wavelength between about 315 nm and about 430 nm. Thus, the third electromagnetic radiation may be disinfecting UV-A radiation that is incorporated into a lighting unit that produces visible light.

In various embodiments, the third wavelength is between about 390 nm and about 420 nm. In various embodiments, the third wavelength is about 405 nm. In various embodiments, the lighting unit consists of the first LED, the second LED, and the third LED. In various embodiments, the lighting unit may further include a circuit board to which the first, second, and third LEDs are mounted. The circuit board may include a fluorescence inhibiting coating. Further, the lighting unit may include one or more lenses for covering the LEDs, the diffuser lens(es) may include at least one of a glass material, a polymethyl methacrylate material, and a polyamide material (e.g., not a polycarbonate material).

Also disclosed herein, according to various embodiments, is a lighting assembly that includes at least one lighting unit and circuitry. The at least one lighting unit may be as described above, and the circuitry may be electrically coupled to the at least one lighting unit and may be configured to drive relative intensity outputs of the respective LEDs of the least one lighting unit. In various embodiments, the lighting assembly further includes a controller electrically coupled to the circuitry (which may be collectively referred to as a lighting system). The controller may include a processor and a tangible, non-transitory computer-readable storage medium having instructions stored thereon that, in response to execution by the processor, cause the processor to perform various operations. The various operations may include controlling, by the processor, the relative intensity outputs of the respective LEDs.

In various embodiments, controlling the relative intensity outputs comprises blending the first electromagnetic radiation, the second electromagnetic radiation, and the third electromagnetic radiation to emit white light from the at least one lighting unit. In various embodiments, the operations comprise determining, by the processor, a dosage of disinfecting electromagnetic radiation from the third LED. Determining, by the processor, the dosage of the disinfecting electromagnetic radiation may include calculating, by the processor, a disinfection rating of an environment where the lighting assembly is situated. Calculating, by the processor, the disinfection rating may be based on at least one of an intensity of the third electromagnetic radiation, an activated time of the third LED, and a distance between the at least one light unit and a target surface of the environment that is susceptible to indirect contact transmission of pathogens. The disinfection rating may pertain to at least one of a planned disinfection procedure and a performed disinfection procedure. In various embodiments, the operations comprise recommending supplementary disinfection procedures. In various embodiments, controlling the relative intensity outputs comprises increasing intensity of the third electromagnetic radiation over the first electromagnetic radiation and the second electromagnetic radiation to emit enhanced-disinfecting light.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

Disclosed herein, according to various embodiments, are devices, systems, methods, and articles of manufacture for incorporating a degree of disinfecting electromagnetic radiation into visible light from a lighting unit. Generally, the devices, systems, methods, and articles of manufacture disclosed and described herein facilitate disinfection treatments, specifically to incorporating electromagnetic radiation that can at least partially inactivate or inhibit pathogens, according to various embodiments. Although numerous details and examples are included herein pertaining to utilizing these concepts to aircraft cabins, the present disclosure is not necessarily so limited, and thus aspects of the disclosed embodiments may be adapted for performance in a variety of other industries (e.g., trains, vehicles, buildings, hotels, etc.). As such, numerous applications of the present disclosure may be realized.

Figure 1:
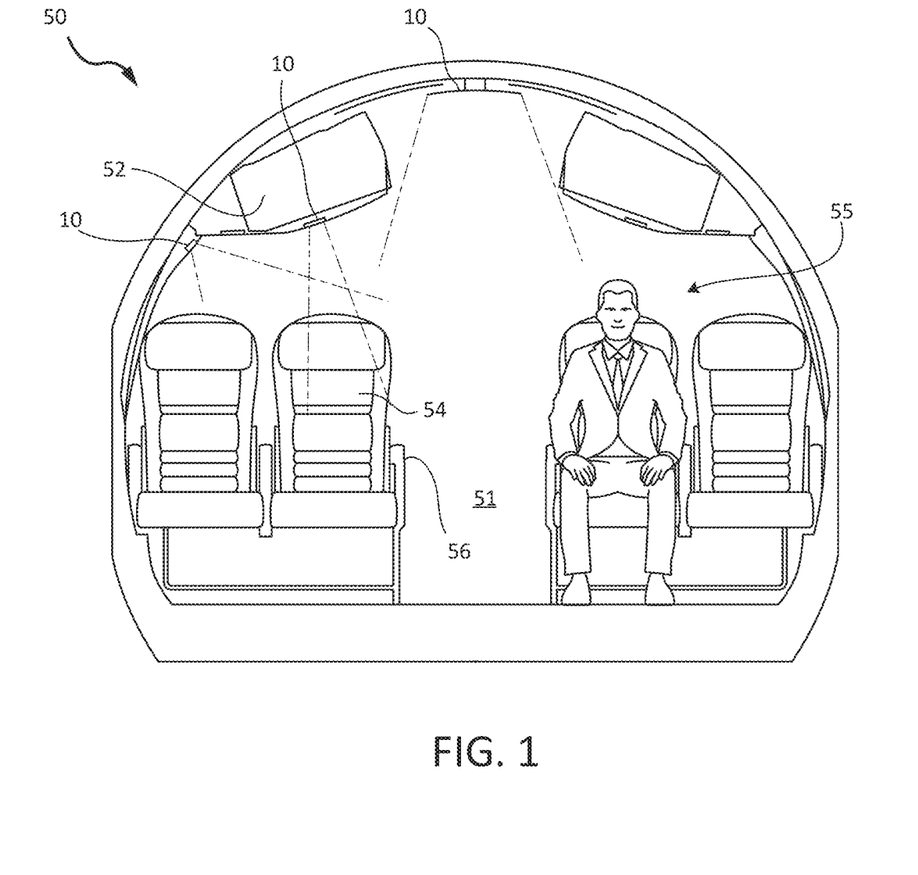
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer or pathogens between passengers, one or more of the lighting systems 10 may blend disinfecting electromagnetic radiation into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft.

Figure 2:
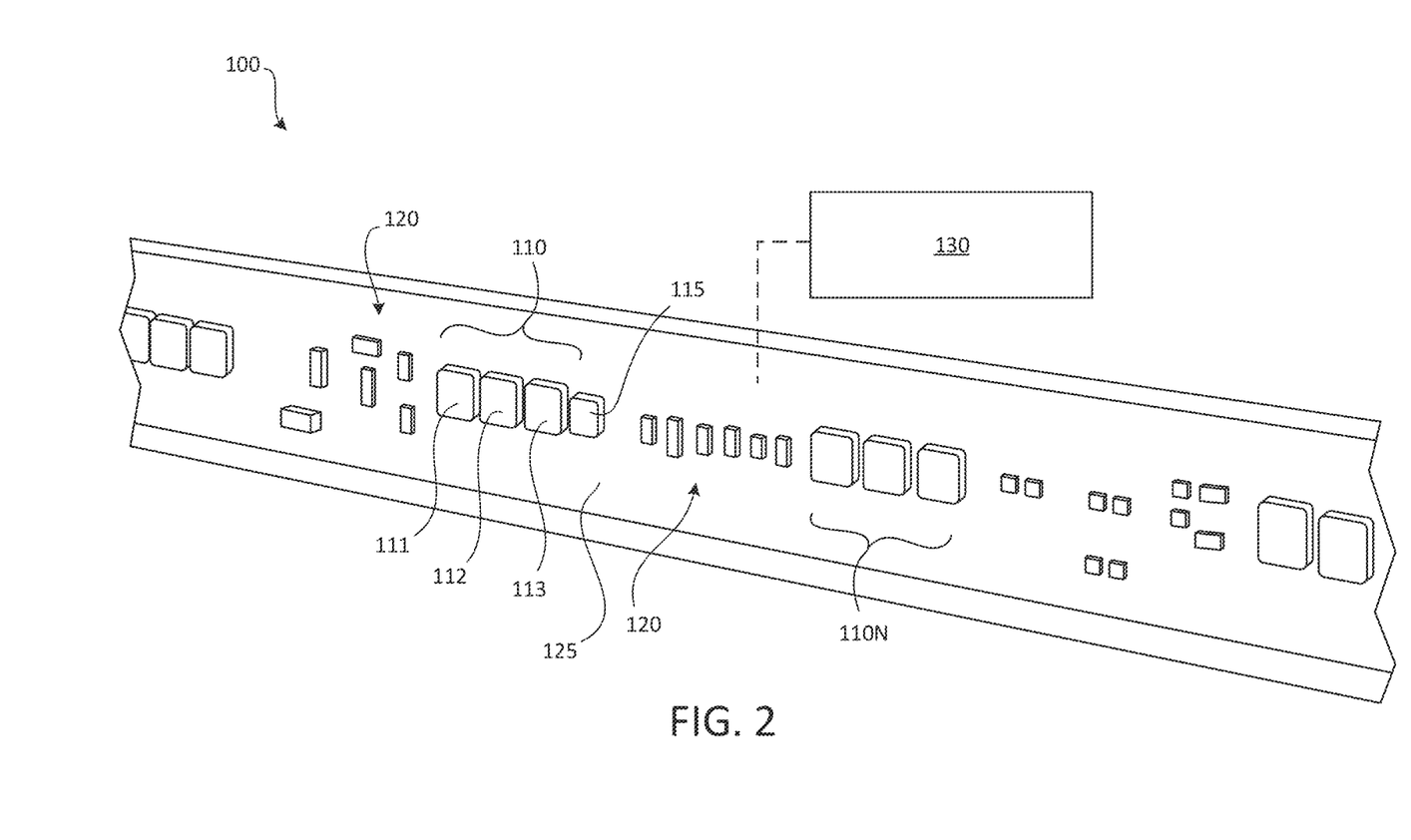
FIG. 2 illustrates a perspective view of a light system including at least one lighting unit, circuity, and a controller, in accordance with various embodiments.

In various embodiments, and with reference to FIG. 2, a lighting system 100 is provided. The lighting system 100 may be one or more of the lighting systems 10 of the aircraft 50 from FIG. 1. The lighting system 100 generally includes a lighting unit 110, circuitry 120, and a controller 130, according to various embodiments. The lighting unit 110, according to various embodiments, includes a specific light-emitting diode ("LED") configured to emit electromagnetic radiation that is at least partially effective at inactivating and/or inhibiting pathogens. With this specific LED incorporated with other standard LEDs, the disinfecting electromagnetic radiation may be masked (i.e., blended) with the other electromagnetic radiation. Additional details pertaining to the lighting unit 110, the circuitry 120, and the controller 130 are provided below.

The term "lighting unit," as used herein, generally refers to an array of discrete LEDs that are controlled to blend their respective radiations to collectively produce a desired hue and intensity of electromagnetic radiation. In various embodiments, the lighting unit 110 include a first LED 111 configured to emit first electromagnetic radiation having a first wavelength of between about 600 nanometers ("nm") and about 740 nm (e.g., red light), a second LED 112 configured to emit second electromagnetic radiation having a second wavelength of between about 500 nm and about 565 nm (e.g., green light), and a third LED 113 (e.g., the 'specific' LED mentioned above) configured to emit third electromagnetic radiation having a third wavelength between about 315 nm and about 430 nm. In various embodiments, the third wavelength is between about 390 nm and about 420 nm. In various embodiments, the third wavelength is about 405 nm. As used in this context only, the term "about" refers to plus or minus 5 nm. Thus, the third LED 113 may emit "long-wave" ultraviolet light, commonly referred to as "UV-A" light, and this third LED 113 may replace a conventional blue LED. This type UV-A light may facilitate a degree of pathogen inactivity and/or inhibition over a conventional blue LED, and thus is referred to herein as "disinfecting electromagnetic radiation," while still being safe for humans. Pathogens may refer to bacteria, viruses, fungal spores, and other microorganisms. In various embodiments, the lighting unit may include more than these three LEDs. For example, the lighting unit may include 4, 5, 6, 7, or 8 LEDs, and these additional LEDs may be other colors, such as amber, cyan, etc.

Figure 3:
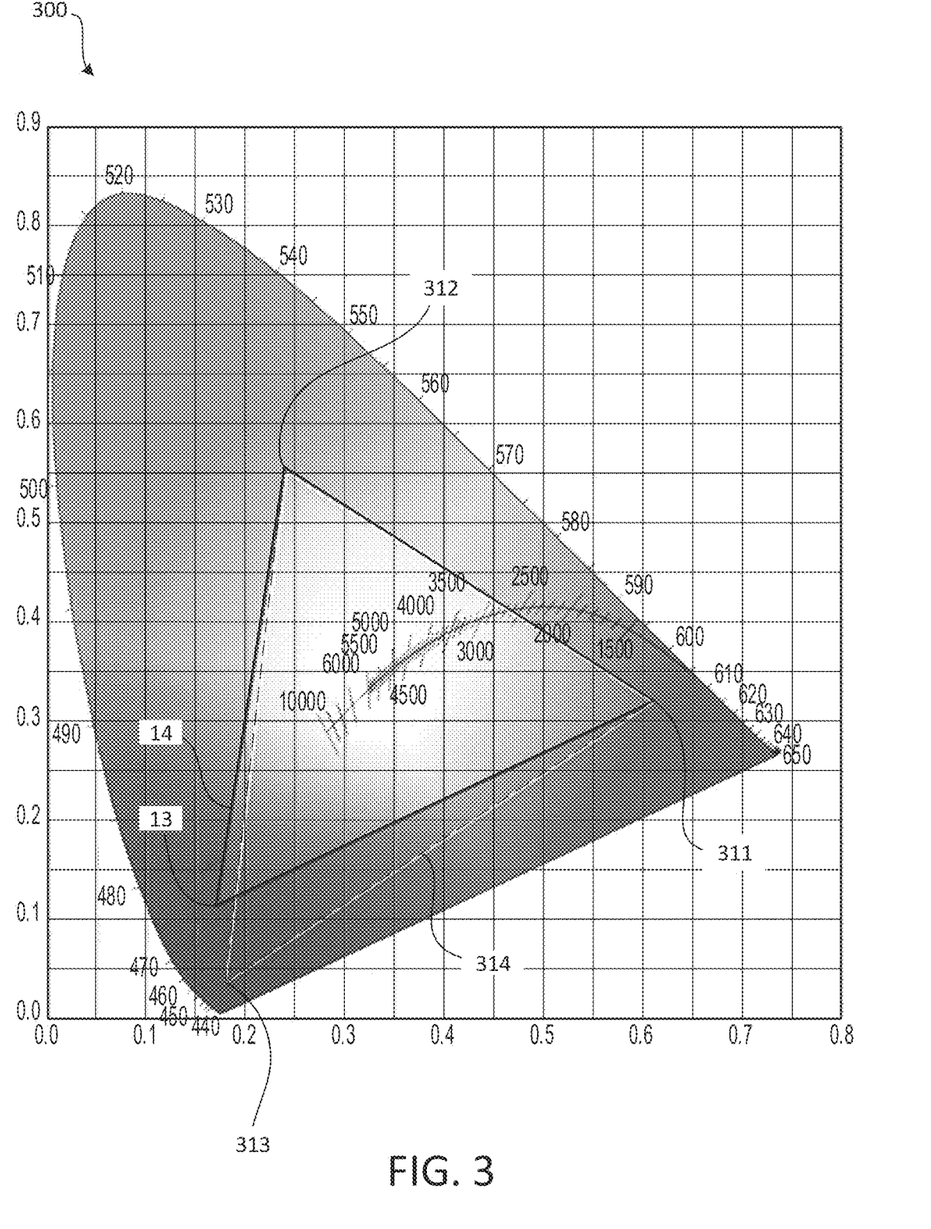
FIG. 3 is a color space chromaticity diagram from the International Commission on Illumination ("CIE"), commonly referred to as a CIE 1931 system diagram, showing various triangular color gamuts, in accordance with various embodiments.
Figure 6:
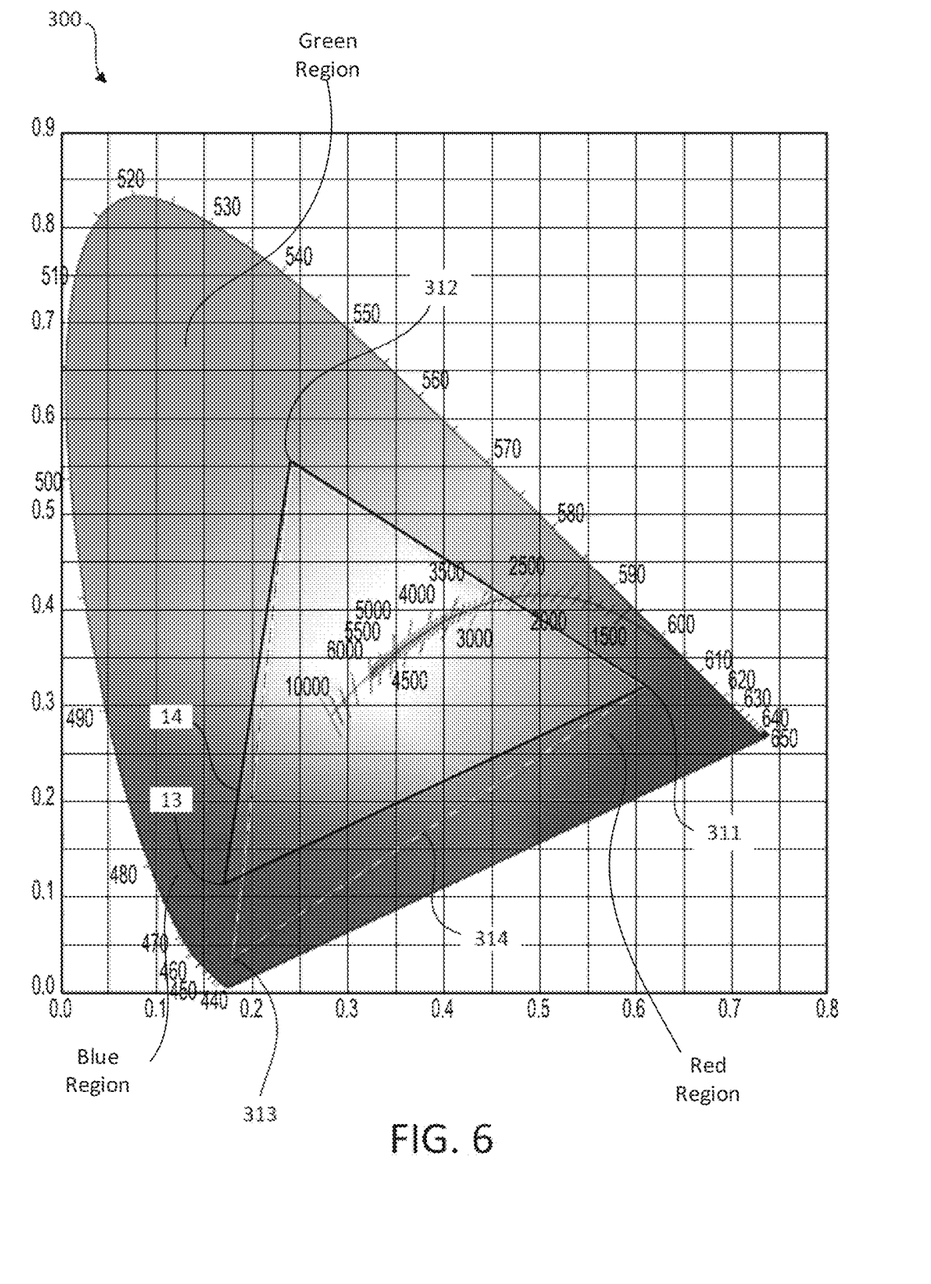
FIG. 6 is a black and white representation of the color space chromaticity diagram of FIG. 3, with various color regions labeled, in accordance with various embodiments.

In various embodiments, and with momentary reference to FIG. 3, a color space chromaticity diagram from the International Commission on Illumination ("CIE"), commonly referred to as a CIE 1931 system diagram 300, is provided. FIG. 6 is a black and white representation of FIG. 3 with various regions of the CIE 1931 system diagram 30 labeled with their respective colors. That is, FIG. 6 is labeled with a red region, a green region, and a blue region. The CIE 1931 system diagram 300 shows a conventional color gamut 14 in which a conventional blue LED 13 is utilized in a conventional lighting unit, and the CIE 1931 system diagram 300 also shows a disinfecting color gamut 314 provided by replacing the conventional blue LED 13 with a specific LED 313 configured to emit disinfecting electromagnetic radiation. Thus, both the conventional color gamut 14 and the disinfecting color gamut 314 may be formed of a first LED 311 and a second LED 312, which may be comparable to the first LED 111 and the second LED 112, respectively referenced above, but the disinfecting color gamut 314 includes LED 313 configured to emit UV-A light as opposed to "blue" light. The shifted, disinfecting color gamut 314 still provides for the collective radiation of the three LEDs 311, 312, 313 to be tuned based on desired color output, as described in greater detail below. That is, the lighting unit 110 may still be controlled to create different lighting schemes within color gamut 314 while including (e.g., masking) UV-A radiation. In various embodiments, if the lighting unit has more than 3 LEDs, the color gamut may be further expanded (e.g., may be referred to as a hyper gamut and may comprise, for example 6 LEDs). Thus, the lighting unit 110 disclosed herein generally replaces a conventional "blue" light with the UV-A light.

Returning to reference FIG. 2, the circuitry 120 of the lighting system 100 may include a circuit board 125 and may generally include various integrated circuit components which may carry out a variety of functions under the control of the controller 130. In various embodiments, the combination of the lighting unit 110 and the circuitry 120 is referred to as a lighting assembly, and the lighting assembly is configured to be driven/controlled by the controller 130, as described in greater detail below. The particular implementations shown and described herein are illustrative examples of an LED lighting assembly, and are thus not intended to otherwise limit the scope of the present disclosure in any way. For the sake of brevity, conventional electronics other components of the circuitry (such as power supplies and power modulators) may not be described in detail. The circuitry 120 is electrically coupled to the lighting unit 110 to supply respective driving signals to each of the LEDs 111, 112, 113. In various embodiments, the lighting unit 110 may include additional LEDs, such as a white LED 115. In various embodiments, the lighting unit consists of only the three LEDs 111, 112, 113 described above, and thus may not include other LEDs. The lighting unit 110 may be replicated/repeated along a strip of circuit board 125. In various embodiments, the circuitry 120 and/or the circuit board 125 includes a fluorescence inhibiting coating that is configured to decrease fluorescence of the circuit board in response to the UV-A radiation. In various embodiments, the lighting unit 110 may include a diffuser lens (or diffuser lenses) covering the LEDs 111, 112, 113, and these lens(es) may comprise a glass material, a polymethyl methacrylate material, and/or a polyamide material, among others. In various embodiments, these lens(es) are not made from polycarbonate materials, as UV-A radiation may not transmit well through such materials.

In various embodiments, and with continued reference to FIG. 2, the controller 130 of the light system 100 may be affixed/integrated into the circuitry 120 or the controller 130 may be integrated into computer systems onboard an aircraft. The controller 130 in FIG. 2 is shown schematically, and thus the size, position, and orientation of the controller may be different than what is depicted in FIG. 2. In various embodiments, the controller 130 comprises a processor. In various embodiments, the controller 130 is implemented in a single processor. In various embodiments, the controller 130 may be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. The controller 130 may comprise a processor configured to implement various logical operations in response to execution of instructions, for example, instructions stored on a non-transitory, tangible, computer-readable medium (i.e., the memory) configured to communicate with the controller 130. Furthermore, any number of conventional techniques for electronics configuration, signal processing and/or control, data processing and the like may be employed. Also, the processes, functions, and instructions may can include software routines in conjunction with processors, etc.

System program instructions and/or controller instructions may be loaded onto a non-transitory, tangible, computer-readable medium having instructions stored thereon that, in response to execution by the processor, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory of the controller 130 may be configured to perform various operations. The schematic flow chart diagrams of FIGS. 4 and 5 include various exemplary controller methods 490, 590 that the processor of the controller 130 may perform. Generally, the controller 130 electrically coupled to the circuitry 120 and is configured to control, by the processor, the relative intensity outputs of the respective LEDs 111, 112, 113 of the lighting unit 110, according to various embodiments. Controlling the relative intensity outputs of the LEDs 111, 112, 113 may include blending the first electromagnetic radiation, the second electromagnetic radiation, and the third electromagnetic radiation to emit a specific color scheme, such as white light, from the lighting unit (or from multiple lighting units forming a region/module of lights). In various embodiments, the operations performed by the controller may include determining a dosage of disinfecting electromagnetic radiation from the third LED 113.

Figure 4:
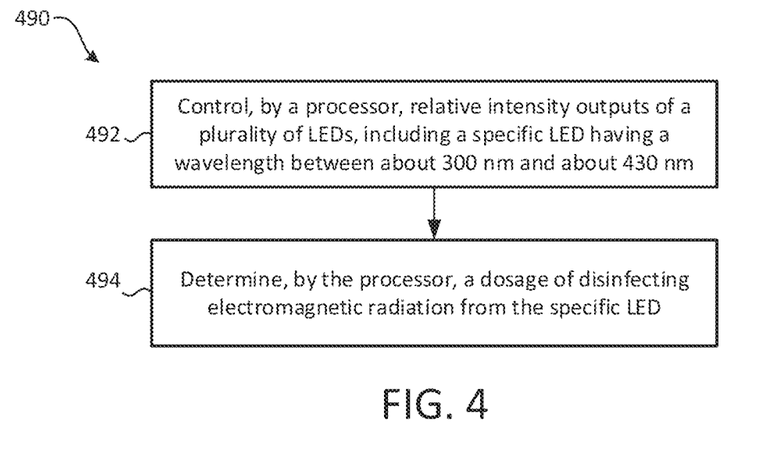
FIG. 4 is a schematic flow chart diagram showing a controller method, in accordance with various embodiments.
Figure 5:
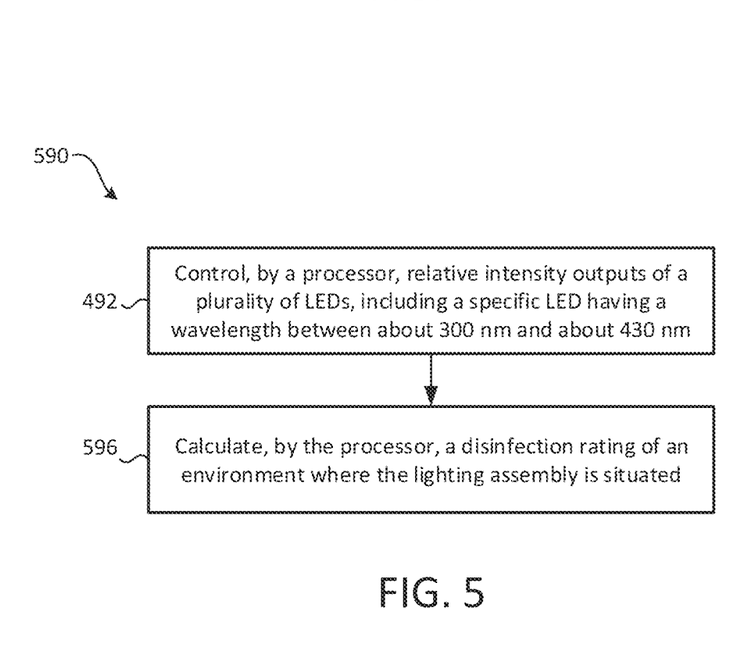
FIG. 5 is a schematic flow chart diagram showing a controller method, in accordance with various embodiments.

For example, and with reference to controller method 490 of FIG. 4, the controller may be configured to control the relative intensity outputs of a plurality of LEDs at step 492 and determining the dosage of disinfecting electromagnetic radiation from one of LEDs (e.g., the third LED that is configured to emit UV-A) at step 494. In various embodiments, and with reference to FIG. 5, the controller method 590 includes include calculating, by the processor, a disinfection rating of an environment where the lighting assembly is situated. The disinfection rating may be based on at least one of an intensity of the third electromagnetic radiation, an activated time of the third LED (e.g., to account for how long the disinfecting UV-A light has been irradiated at target surfaces and/or to account for luminance degradation over time), and a distance between the light unit 110 and a target surface of the environment that is susceptible to indirect contact transmission of pathogens. The term "disinfection rating" may refer to a planned disinfection procedure (i.e., an estimated quantification of the extent of a disinfection treatment that will be carried out) or may refer to a performed disinfection procedure (i.e., an estimated quantification of the cleanliness of the environment after a disinfection treatment has been performed). In various embodiments, the operations performed by the controller 130 include recommending supplementary disinfection procedures. That is, if the lighting unit 110 was not activated for a sufficient time period, the aircraft may require supplemental/extra disinfection to meet cleanliness thresholds. Accordingly, the controller 130 may communicate an alert or other notification to an aircraft crew member or other maintenance operator. In various embodiments, the controller 130 may actively modulate the light blending in order to meet threshold cleanliness levels. For example, the controller 130 may be configured to increase the intensity of the third LED 113

(e.g., more than that of the first and second LEDs 111, 112) between flights or during portions of a flight when not as much visible white light may be necessary, thus increasing the disinfection intensity of the UV-A light (i.e., enhanced-disinfecting light).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A lighting assembly comprising:
    a lighting unit comprising:
        a first light-emitting diode ("LED") configured to emit first electromagnetic radiation having a first wavelength of between about 600 nanometers ("nm") and about 740 nm;
        a second LED configured to emit second electromagnetic radiation having a second wavelength of between about 500 nm and about 565 nm; and
        a third LED configured to emit third electromagnetic radiation having a third wavelength between about 315 nm and about 430 nm;
    circuitry electrically coupled to the lighting unit and configured to drive relative intensity outputs of the respective LEDs of the lighting unit; and
    a controller electrically coupled to the circuitry, the controller comprising a processor and a tangible, non-transitory computer-readable storage medium having instructions stored thereon that, in response to execution by the processor, cause the processor to perform various operations comprising:
        controlling, by the processor, the relative intensity outputs of the respective LEDs;
        calculating, by the processor, a disinfection rating of an environment where the lighting assembly is situated using an intensity of the third electromagnetic radiation, an activated time of the third LED, and a distance between the lighting unit and a target surface of the environment that is susceptible to indirect contact transmission of pathogens, wherein the disinfection rating comprises a planned disinfection procedure and an estimated cleanliness of the environment after a performed disinfection procedure; and
        recommending, by the processor, supplementary disinfection procedures if the estimated cleanliness of the environment fails to meet a cleanliness threshold.

2. The lighting assembly of claim 1, wherein controlling the relative intensity outputs comprises blending the first electromagnetic radiation, the second electromagnetic radiation, and the third electromagnetic radiation to emit white light from the lighting unit.

3. The lighting assembly of claim 1, wherein the operations comprising determining, by the processor, a dosage of disinfecting electromagnetic radiation from the third LED.

4. The lighting assembly of claim 1, wherein controlling the relative intensity outputs comprises increasing intensity of the third electromagnetic radiation over the first electromagnetic radiation and the second electromagnetic radiation to emit enhanced-disinfecting light.

5. A lighting system for an aircraft, the lighting system comprising:
at least one lighting unit disposed in a cabin of the aircraft, the at least one lighting unit comprising:
a first light-emitting diode ("LED") configured to first emit electromagnetic radiation having a first wavelength of between about 600 nanometers ("nm") and about 740 nm;
a second LED configured to emit second electromagnetic radiation having a second wavelength of between about 500 nm and about 565 nm; and
a third LED configured to emit third electromagnetic radiation having a third wavelength between about 315 nm and about 430 nm;
circuitry electrically coupled to the at least one lighting unit and configured to drive relative intensity outputs of the respective LEDs of the least one lighting unit; and
a controller electrically coupled to the circuitry, the controller comprising a processor and a tangible, non-transitory computer-readable storage medium having instructions stored thereon that, in response to execution by the processor, cause the processor to perform various operations comprising controlling, by the processor, the relative intensity outputs of the respective LEDs, calculating, by the processor, a disinfection rating of an environment where the lighting assembly is situated using an intensity of the third electromagnetic radiation, an activated time of the third LED, and a distance between the lighting unit and a target surface of the environment that is susceptible to indirect contact transmission of pathogens, wherein the disinfection rating comprises a planned disinfection procedure and an estimated cleanliness of the environment after a performed disinfection procedure; and recommending, by the processor, supplementary disinfection procedures if the estimated cleanliness of the environment fails to meet a cleanliness threshold.

6. The lighting system of claim 5, wherein the at least one lighting unit comprises a plurality of lighting units, wherein LEDs of each lighting unit of the plurality of lighting units consists of the first LED, the second LED, and the third LED.

7. The lighting system of claim 5, wherein the third wavelength is about 405 nm.

* * * * *

UNITED STATES PATENT AND TRADEMARK OFFICE
CERTIFICATE OF CORRECTION

| | |
|---|---|
| PATENT NO. | : 11,480,329 B2 |
| APPLICATION NO. | : 17/027496 |
| DATED | : October 25, 2022 |
| INVENTOR(S) | : John Edquist et al. |

It is certified that error appears in the above-identified patent and that said Letters Patent is hereby corrected as shown below:

On the Title Page

Item (72) Inventors: after "John Edquist" please delete "Miwaukee" and insert --Milwaukee--

Signed and Sealed this
Twenty-eighth Day of March, 2023

Katherine Kelly Vidal
*Director of the United States Patent and Trademark Office*